United States Patent
Blake

[11] Patent Number: 5,944,729
[45] Date of Patent: Aug. 31, 1999

[54] VASCULAR OCCLUSION CLAMP WITH RADIOPAQUE RETRIEVAL, IDENTIFICATION AND MARKING STRING

[75] Inventor: Kenneth R. Blake, Brooklyn Park, Minn.

[73] Assignee: Scanlan International, Inc., St. Paul, Minn.

[21] Appl. No.: 08/989,524

[22] Filed: Dec. 12, 1997

[51] Int. Cl.[6] .................................................. A61B 17/10
[52] U.S. Cl. ........................ 606/139; 606/205; 606/210; 606/194; 604/4; 604/53
[58] Field of Search .................................. 606/139, 205, 606/210, 194; 604/4, 53

[56] References Cited

U.S. PATENT DOCUMENTS

| D. 268,523 | 4/1983 | Sacanlan, Jr. et al. | D24/27 |
|---|---|---|---|
| D. 276,461 | 11/1984 | Sacanlan, Jr. et al. | D24/27 |
| 1,741,457 | 12/1929 | Glass . | |
| 2,046,781 | 7/1936 | Head | 24/261 |
| 2,890,519 | 6/1959 | Storz, Jr. | 29/225 |
| 3,274,658 | 9/1966 | Pile | 24/259 |
| 3,746,002 | 7/1973 | Haller | 128/322 |
| 3,805,792 | 4/1974 | Cogley | 128/325 |
| 3,827,438 | 8/1974 | Kees, Jr. | 128/346 |
| 3,868,957 | 3/1975 | Doddington | 128/346 |
| 3,996,937 | 12/1976 | Williams | 128/325 |
| 4,024,868 | 5/1977 | Williams | 128/325 |
| 4,531,519 | 7/1985 | Dunn et al. | 128/327 |
| 4,542,743 | 9/1985 | Dunn et al. | 128/327 |
| 4,708,140 | 11/1987 | Baron | 128/325 |
| 4,827,929 | 5/1989 | Hodge | 128/321 |
| 5,019,092 | 5/1991 | Klintmalm | 606/207 |
| 5,042,118 | 8/1991 | Rubik | 24/523 |
| 5,133,724 | 7/1992 | Wilson, Jr. et al. | 606/151 |
| 5,282,812 | 2/1994 | Suarez, Jr. | 606/158 |
| 5,769,812 | 6/1998 | Stevens et al. | 606/194 |
| 5,800,455 | 9/1998 | Palermo et al. | 606/191 |
| 5,810,757 | 9/1998 | Sweezer, Jr. et al. | 604/4 |
| 5,833,682 | 11/1998 | Amplatz et al. | 606/15 |
| 5,855,577 | 1/1999 | Murphy-Chutorian et al. | 606/15 |

Primary Examiner—Michael Buiz
Assistant Examiner—(Jackie) Tan-Uyen T. Ho
Attorney, Agent, or Firm—Faegre & Benson LLP

[57] ABSTRACT

A radiopaque marked vascular clamp comprises a vascular clamp with a radiopaque string attached thereto. The clamp is a cross-action spring clamp constructed as a single-piece body. The clamp has first and second opposing elongated members. Each member has a proximal end, a mid-point and a distal end. Each member has a first section between its proximal end and a point just proximal of its mid-point, and a second section between a point just proximal of its mid-point and its distal end. The members are hinged to each other at their proximal ends. The first section of each member curves away from its opposing member along the first section, so that the proximal ends are relatively closer to each other and the points just proximal of the mid-points are relatively farther away from each other. The first and second members cross over each other at their mid-points. The second section of each member is formed with a jaw surface, so that the jaw surfaces are normally biased in clamping contact with each other and are urged away from each other by pressure applied to move the first sections toward each other. The radiopaque string is attached to the clamp and is sized and adapted to increase X-ray visibility of the clamp.

18 Claims, 2 Drawing Sheets

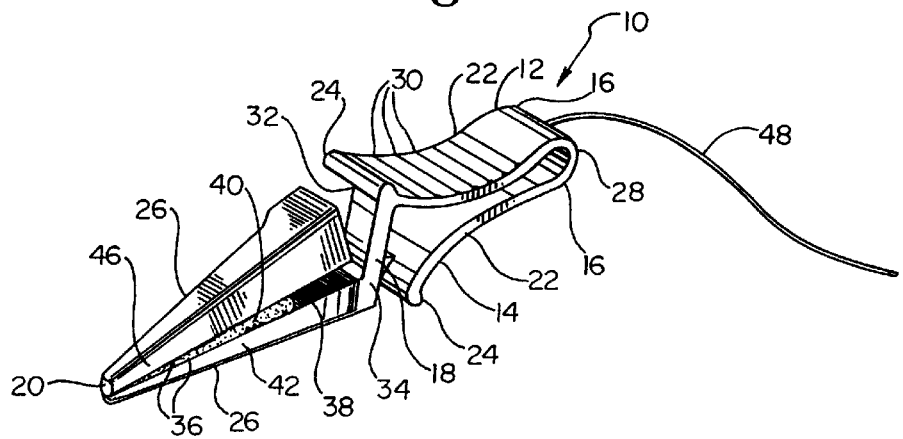
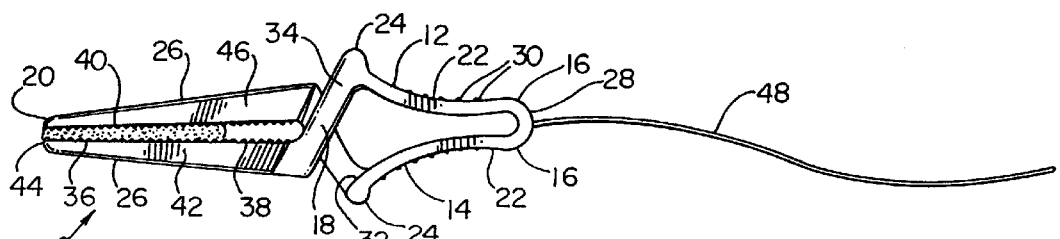
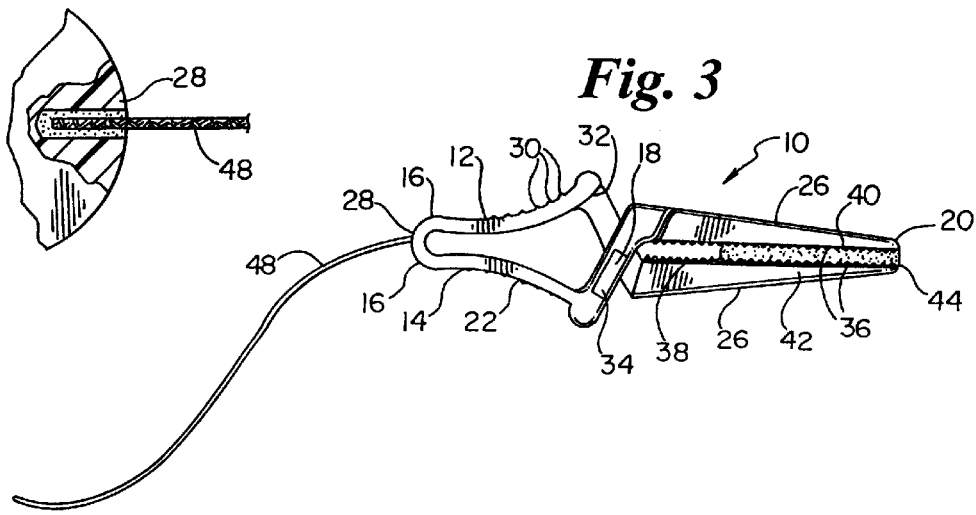

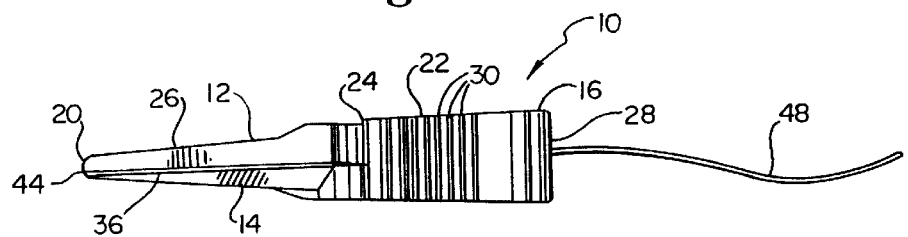
Fig. 4
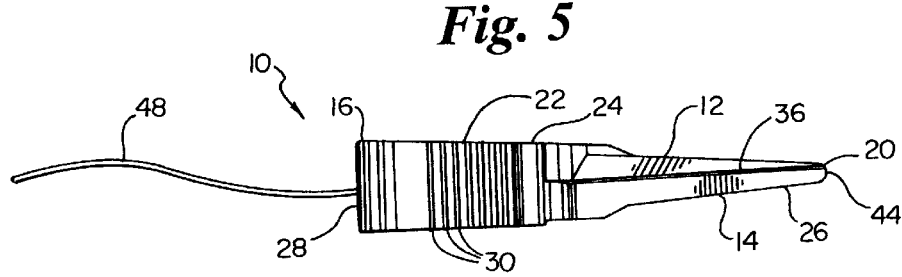
Fig. 5
Fig. 6
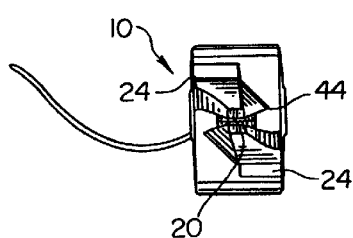
Fig. 7
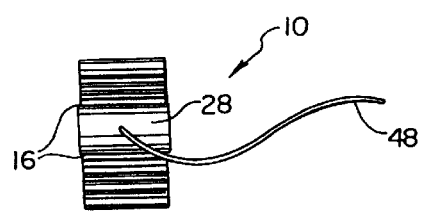
Fig. 8
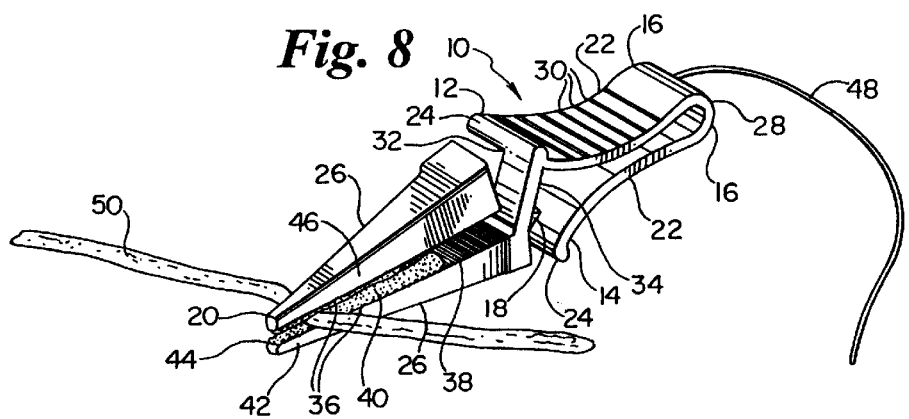

VASCULAR OCCLUSION CLAMP WITH RADIOPAQUE RETRIEVAL, IDENTIFICATION AND MARKING STRING

FIELD OF THE INVENTION

This invention relates to a vascular occlusion clamp having attached thereto a radiopaque retrieval, identification, and marking string. More broadly, this invention relates to a surgical instrument having attached thereto a radiopaque marking string.

BACKGROUND OF THE INVENTION

Vascular occlusion clamps are readily commercially available. Such clamps are used for temporary vascular occlusion during surgical procedures and are generally disposable after use, thus avoiding problems associated with repeated usage, sterilization, storage, and record keeping necessarily connected therewith. The clamps can also be used for other types of surgical grasping and clamping of tissue, veins, arteries, etc. These clamps are generally made of a radiopaque acetal homopolymer or nylon. They are of small size, less than about 5 cm in length, and vary in clamping strength with size from about 20 gms to about 175 gms of clamping pressure. Vascular occlusion clamps are available, inter alia, from the assignee of this invention, Scanlan International, Inc. and are disclosed in U.S. Pat. Nos. D 268,523 and D 276,461, which are hereby incorporated by reference in their entireties.

Because these vascluar occlusion clamps can be relatively small, it can be advantageous to have visual indicia of the location of the clamp other than the clamp itself, particularly because the view of the clamp itself may be obstructed in the surgical field. Further, it can be advantageous to provide a mechanism other than the clamp itself by which the clamp may be maneuvered in, and retrieved from, the surgical field. It can also be beneficial if such a maneuvering, retrieval, and visual identification mechanism is radiopaque. This provides additional x-ray contrast area to mark the location of the clamp or, should the mechanism become separated from the clamp, mark the location of the mechanism. For these reasons, some surgical sponges manufactured of cotton may include a radiopaque string wrapped within the sponge.

Thus, it is desirable to provide some method for easily, safely and readily identifying surgical instruments, such as vascular occlusion clamps within a surgical field. It is further desirable to provide some method to retrieve and maneuver the clamp during a surgical procedure.

SUMMARY OF THE INVENTION

The present invention includes a surgical instrument, such as a vascular occlusion clamp, with a radiopaque string attached thereto. The clamp may be a cross-action spring clamp constructed as a single-piece body. Such a clamp has first and second opposing elongated members. Each member has a proximal end, a mid-point and a distal end. Each member has a first section between its proximal end and a point just proximal of its mid-point, and a second section between a point just proximal of its mid-point and its distal end. The members are hinged to each other at their proximal ends. The first section of each member curves away from its opposing member along the first section, so that the proximal ends are relatively closer to each other and the points just proximal of the mid-points are relatively farther away from each other. The first and second members cross over each other at their mid-points. The second section of each member is formed with a jaw surface, so that the jaw surfaces are normally biased in clamping contact with each other and are urged away from each other by pressure applied simultaneously to move the first sections toward each other. The radiopaque string is attached to and extends from the clamp.

BRIEF DESCRIPTION OF THE DRAWINGS

FIG. 1 is a perspective view of the vascular occlusion clamp with a radiopaque marking string of this invention.

FIG. 2 is a left side elevational view of the clamp of FIG. 1.

FIG. 3 is a right side elevational view of the clamp of FIG. 1.

FIG. 4 is a top plan view of the clamp of FIG. 1.

FIG. 5 is a bottom plan view of the clamp of FIG. 1.

FIG. 6 is a front elevational view of the clamp of FIG. 1.

FIG. 7 is a rear elevational view of the clamp of FIG. 1.

FIG. 8 is a perspective view of the clamp of FIG. 1, showing the invention in use to clamp a section of body tissue.

FIG. 9 is a cut-away detail showing the radiopaque string retained within the clamp.

DETAILED DESCRIPTION OF THE INVENTION

FIG. 1 is a perspective view of the vascular occlusion clamp 10 with a radiopaque marking string according to this invention. A radiopaque marked clamp 10, as seen in FIGS. 1–8. comprises a cross-action spring clamp constructed as a single-piece body with first and second opposing elongated members 12, 14. Each member 12, 14 has a proximal end 16, a mid-point 18 and a distal end 20. Each member 12, 14 also has a first gripping section 22, between its proximal end 16 and a point 24 just proximal of its mid-point 18, and a second section 26, between the point 24 just proximal of its mid-point 18 and its distal end 20. The members 12, 14 are hinged to each other at their proximal ends 16 by means of a living spring hinge 28 shaped in one piece with the clamp and having the same material thickness and width as the proximal ends 16 of the members 12, 14.

The first gripping section 22 of the first member 12, as seen in FIGS. 1–3 and 8, curves away from its opposing member 14 along the length of the first gripping section 22, so that the proximal ends 16 are relatively closer to each other and the points 24, just proximal of the mid-points 18, are relatively farther away from each other. The exterior surface of the first gripping sections 22 is roughened such as by being shaped with ribs 30 to ensure secure non-slip gripping by fingers or a gripping tool, such as an applier (in the nature of an oversized elongate tweezers having clawed ends) available from Scanlan International. Inc. of St. Paul, Minn. identified by the mark Scanlan Vascu Statt®. Such a gripping tool or device places the clamp 10 into position in the body and securely holds the jaws 26 of the clamp 10 open by engagement with the gripping sections 22. When the device 10 is removed from the gripping sections 22, the jaws 26 close.

The first gripping section 22 terminates in a hilt at a point 24 just proximal of the mid-point 18 so that the hilts at the points 24 are relatively farther from each other than the remainder of the members 12 and 14. At the hilt at the point 24, the width of each member 12, 14 is reduced by a relief 32 to form a neck 34 of about one-half the width of the first gripping section 22. The necks 34 cross over each other at the mid-points 18. Because of the reduction in width of the necks 34 by the relief 32, the necks 34 cross over each other with minimum contact.

Each second section 26 is shaped so that the facing jaw surface 36 of the first member 12 is in clamping contact with the facing jaw surface 36 of the second opposing member 14. The facing jaw surfaces 36 may be molded with a transverse knurl 38, to ensure secure atraumatic clamping, and may be provided with a foam layer 40, to further reduce trauma to clamped vessels 50 (see FIG. 8). The side wall 42 of the second section 26, perpendicular to the jaw surface 36 and aligned with the neck 34, is relatively straight from the neck 34 to the nose 44 at the distal end 20 of that member 12 (14). The opposing side wall 46 of the second section 26, forms an angle of less than 90° with the jaw surface 36, so that the opposing side wall 46 of one member 12 slopes away from the straight side wall 42 of the other member 14. Optionally, the jaws 36 may be bent at an angle along their length (not shown) to facilitate ease of positioning within the body.

The jaw surfaces 36 are normally biased in clamping contact with each other and are urged away from each other by pressure applied simultaneously to the ribbed gripping first sections 22 to move the first sections 22 toward each other. Because of the relief 32 forming the neck 34 of reduced width and the hilt at the point 24 just proximal of the mid-point 18 of either member, when pressure is applied to the first sections 22, the extent of opening of the jaw surfaces 36 is limited by the neck 34 of one member 12 confronting the hilt of the second member 14.

A radiopaque string 48 extends from the living spring hinge 28 of the clamp 10. To attach the string 48 to the clamp 10, a hole is drilled through the living spring hinge 28 and the string 48 is secured therein by means of an adhesive bond, such as an epoxy adhesive, as can be seen in FIG. 9. The string 48 may be formed of a flexible material. Such a material may also be resiliently extensible. The string 48 may be resiliently extensible to permit, via the string 48, placement, withdrawal, or a maneuvering of the clamp 10. For example, this resiliently extensible feature permits a slight tugging on the tail 48 so as to permit the surgeon to gauge the resistance offered by the clamp 10 when it is in place without disengaging the clamp 10 from the blood vessel.

The length of the marking string 48 is preferably that which provides for easy identification, retrieval and maneuvering of the clamp 10 during use, such as during a surgical procedure. More preferably, the string is about 6 to about 24 inches in length. If desired, the string 48 may be equal to or greater than an elongate length of the clamp 10. The diameter of the string 48 is preferably that which provides adequate radiopacity, strength, and easy visualization. More preferably, the diameter of the string 48 is about 0.093 to about 0.125 inches. Generally, the material of the adhesive and of the string 48 are chosen so that the strength of the adhesive bond between the string 48 and the hinge 28 is greater than the tensile strength of the string 48. This ensures that, as pulling pressure on the string 48 increases, the string 48 will break before the string 48 can be pulled out of the hinge 28.

The radiopaque marking string 48 serves two purposes. First, the string 48 provides an opportunity for the user to easily keep track of the attached clamp (or other surgical instrument) within the surgical field and provides a means by which the clamp (or other surgical instrument) can be withdrawn prior to closing the surgical site. Second, the string 48 improves radiopacity by providing a larger radiopaque target.

The body of the clamp 10 is preferably formed from a biocompatible polymer or copolymer, more preferably a radiopaque biocompatible polymer or copolymer, and most preferably a radiopaque acetal homopolymer or nylon. The string 48 is preferably formed from a biocompatible polymer or copolymer with a radiopaque material embedded therein, more preferably a polyvinyl chloride with a radiopaque material embedded therein, and most preferably a polyvinyl chloride with a USP barium sulfate additive to render the string 48 radiopaque. If desired, the body of the clamp 10 and the tail or string 48 may be formed of the same polymer and copolymer and may be integral with each other.

To retain a section of tissue or blood vessel 50; pressure is applied to the first sections 22 to move the first sections 22 toward each other and to simultaneously move the jaw surfaces 36 away from each other. The extent of opening of the jaw surfaces 36 is limited by the neck 34 of one member 12 confronting the hilt at the point 24 of the second member 14. With the jaw surfaces 36 in the open position, a section of tissue or blood vessel 50 is positioned between the jaw surfaces 36. Pressure on the first sections 22 is released allowing the first sections 22 to move away from each other and to simultaneously allow the jaw surfaces 36 to firmly and securely clamp upon the section of tissue or blood vessel 50. To release the section of tissue or blood vessel 50 from the jaw surfaces 36, pressure is again applied to the first sections 22.

It can be appreciated that the present radiopaque marked surgical instrument is preferably a surgical instrument that is sufficiently small to be introduced into a patient's body during a surgical procedure and that is a stand alone instrument such that the instrument is capable of performing a surgical function without the aid of any other instrument. It can be further appreciated that the string or tail 48 is engaged to an end of the instrument which is spaced from the structure performing the surgical function.

It can be noted that the clamp 10 includes a first end with a pair of jaws 26 swingable with respect to each other and normally biased to confront each other to perform the surgical function and further includes a second end with a pair of arms 22 resiliently drawable together to operate the first end and normally biased apart from each other.

It can be further appreciated that the clamp 10 is preferably of a size smaller than 5 cm in length, and preferably has a clamping pressure from about 20 gms to about 175 gms.

Although the present invention has been described with reference to preferred embodiments, those skilled in the art will recognize that changes can be made in form and detail without departing from the spirit and scope of the invention.

What is claimed is:

1. A radiopaque marked clamp comprising:
   a cross-action spring clamp constructed as a single-piece body with first and second opposing elongated members;
   each member having a proximal end, a mid-point and a distal end, each member having a first section between its proximal end and a point just proximal of its mid-point, and a second section between a point just proximal of its mid-point and its distal end;
   said members joined to each other through a hinge at their proximal ends;
   each first section curving away along its length from its opposing member, so that the proximal ends are relatively closer to each other and the points just proximal of the mid-points are relatively farther away from each other;

the first and second members crossing over each other at their mid-points;

the distal end of each second section shaped with a clamping jaw surface, so that the jaw surface of the first member is in clamping contact with the facing jaw surface of the second opposing member;

such that the jaw surfaces are normally biased in clamping contact with each other and are urged away from each other by pressure applied to move the first sections toward each other; and a radiopaque string attached to the clamp, said string sized and adapted to increase X-ray visibility of the clamp.

2. A clamp according to claim 1, wherein the string is attached to the clamp by means of an adhesive bond between the string and the hinge.

3. A clamp according to claim 2, wherein the strength of the adhesive bond between the string and the hinge is greater than the tensile strength of the string.

4. A clamp according to claim 1, and further including a pilot hole in the hinge and wherein the string is a resilient extensible string secured into the pilot hole by means of an adhesive bond.

5. A clamp according to claim 1, wherein each of the jaw surfaces are further provided with a foam cushion.

6. A clamp according to claim 1, wherein the clamp is constructed of acetal homopolymer or nylon.

7. A clamp according to claim 1, wherein the string is constructed of radiopaque PVC.

8. A radiopaque marked surgical cross-action spring vascular occlusion clamp comprising:

a surgical cross-action spring vascular occlusion clamp of a size and type to be introduced into a patient's body during a surgical procedure; and a radiopaque strand attached to and extending from the surgical clamp, said strand sized and adapted to increase X-ray visibility of the clamp.

9. A radiopaque marked surgical clamp according to claim 8, and further including an adhesive bond between the strand and the surgical clamp.

10. A radiopaque marked surgical clamp according to claim 9, wherein the strength of the adhesive bond between the strand and the surgical clamp is greater than the tensile strength of the strand.

11. A radiopaque marked surgical clamp according to claim 8, wherein the clamp is of acetal homopolymer or nylon.

12. A radiopaque marked surgical lamp according to claim 8, wherein the strand is of radiopaque polyvinyl chloride with a USP barium sulfate additive.

13. A radiopaque marked surgical instrument comprising:

a surgical instrument comprising first and second ends, the first end including a pair of jaws swingable with respect to each other and normally biased to confront each other to perform a surgical function, and the second end being structured to operate the first end, the surgical instrument being sufficiently small to be introduced into a patient's body during a surgical procedure;

with the surgical instrument being a stand alone instrument such that the instrument is capable of performing a surgical function without the aid of any other instrument; and with a radiopaque strand engaged to and extending from the second end of the surgical instrument and further extending away from and out of the way of the first end which performs the surgical function whereby the X-ray visibility of the surgical instrument is increased.

14. A radiopaque marked surgical instrument according to claim 13 wherein the second end comprises arms resiliently drawable together to operate the first end and normally biased apart from each other.

15. A radiopaque marked surgical instrument according to claim 13 wherein the strand is flexible and resiliently extensible.

16. A radiopaque marked surgical instrument according to claim 13 wherein the strand is formed of a polymer, with a radiopaque material embedded in the polymer.

17. A radiopaque marked surgical instrument according to claim 13 wherein the first end comprises portions which engage tissue, with the portions comprising foam to reduce trauma to tissue.

18. A radiopaque marked surgical instrument comprising:

a surgical instrument being sufficiently small to be introduced into a patient's body during a surgical procedure, with the surgical instrument having a length;

with the surgical instrument having first and second ends formed of a polymer or copolymer and being intearal with each other, with the first end being structured to perform the surgical function and with the second end being structured to operate the first end, and with the second end further having a roughened surface whereby the second end may be relatively easily encaged by fingers or tools when the surgical instrument is inserted into the body, operated in the body, or withdrawn from the body; and with a flexible tail formed of a polymer or copolymer and engaged to and extending from the second end of the surgical instrument and further extending away from and out of the way of the first end which performs the surgical function, with the length of the tail being equal to or greater than the length of the surgical instrument, and with the tail having a radiopaque material embedded therein such that X-ray visibility of the surgical instrument is increased.

* * * * *

UNITED STATES PATENT AND TRADEMARK OFFICE
CERTIFICATE OF CORRECTION

PATENT NO. : 5,944,729
DATED : August 31, 1999
INVENTOR(S) : Blake

It is certified that error appears in the above-identified patent and that said Letters Patent is hereby corrected as shown below:

Column 6, line 34, delete "intearal" and insert therefor -- integral --

Signed and Sealed this

Ninth Day of May, 2000

Attest:

Q. TODD DICKINSON

Attesting Officer

Director of Patents and Trademarks